United States Patent
Wehbe

(10) Patent No.: US 11,172,912 B2
(45) Date of Patent: Nov. 16, 2021

(54) BIOPSY NEEDLE AND MEDICAL DEVICE INCORPORATING THE SAME

(71) Applicant: Charles Rafic Wehbe, Lakewood, OH (US)

(72) Inventor: Charles Rafic Wehbe, Lakewood, OH (US)

(73) Assignee: INNOVASCI LLC, Lakewood, OH (US)

( * ) Notice: Subject to any disclaimer, the term of this patent is extended or adjusted under 35 U.S.C. 154(b) by 0 days.

(21) Appl. No.: 14/737,405

(22) Filed: Jun. 11, 2015

(65) Prior Publication Data
US 2016/0081673 A1    Mar. 24, 2016

Related U.S. Application Data

(60) Provisional application No. 62/154,646, filed on Apr. 29, 2015, provisional application No. 62/071,374, filed on Sep. 23, 2014.

(51) Int. Cl.
*A61B 10/02* (2006.01)

(52) U.S. Cl.
CPC .. *A61B 10/0266* (2013.01); *A61B 2010/0208* (2013.01)

(58) Field of Classification Search
None
See application file for complete search history.

(56) References Cited

U.S. PATENT DOCUMENTS

| | | | |
|---|---|---|---|
| 4,702,261 A | 10/1987 | Cornell et al. | |
| 5,938,635 A * | 8/1999 | Kuhle | A61M 5/3286 604/272 |
| 5,989,196 A * | 11/1999 | Chu | A61B 10/0275 600/567 |
| 6,416,484 B1 * | 7/2002 | Miller | A61B 10/025 600/564 |
| 6,592,559 B1 | 7/2003 | Pakter et al. | |
| 6,758,824 B1 * | 7/2004 | Miller | A61B 10/025 600/566 |
| 2005/0101984 A1 * | 5/2005 | Chanduszko | A61B 17/0057 606/185 |
| 2006/0167416 A1 | 7/2006 | Mathis et al. | |
| 2007/0055215 A1 * | 3/2007 | Tran | A61B 10/0275 604/540 |
| 2010/0298737 A1 * | 11/2010 | Koehler | A61B 10/0275 600/567 |

(Continued)

OTHER PUBLICATIONS

Singh, et al., "Core Biopsy with Curved Needle Technique", AJR, 2008, pp. 1745-1750, vol. 191.

(Continued)

*Primary Examiner* — Sean P Dougherty
*Assistant Examiner* — Benjamin S Melhus
(74) *Attorney, Agent, or Firm* — Curatolo Sidoti Co., LPA; Floyd Trillis, III

(57) ABSTRACT

Disclosed is a biopsy needle, medical device incorporating the biopsy needle, and method of using the biopsy needle and medical device. The biopsy needle and medical device is used to obtain a sample of tissue for further analysis and testing. The biopsy needle includes an inner stylet that is slidably engaged with an outer coaxial sheath and at least part of the distal portion of the stylet is bent or curved relative to the longitudinal axis of the coaxial sheath.

20 Claims, 6 Drawing Sheets

(56) References Cited

U.S. PATENT DOCUMENTS

| | | |
|---|---|---|
| 2010/0305470 A1 | 12/2010 | Ireland |
| 2012/0220894 A1* | 8/2012 | Melsheimer ....... A61B 10/0275 |
| | | 600/567 |
| 2014/0221870 A1 | 8/2014 | McClellan |
| 2014/0276586 A1* | 9/2014 | Swaney ............. A61B 17/3403 |
| | | 604/506 |
| 2014/0350417 A1* | 11/2014 | Van Bladel .......... A61B 5/0215 |
| | | 600/486 |

OTHER PUBLICATIONS

Karam, et al., "Curved Stylet Core Biopsy Results in Larger Cores", AJR, 2010, pp. 242-244, vol. 195.

* cited by examiner

BIOPSY NEEDLE AND MEDICAL DEVICE INCORPORATING THE SAME

CROSS REFERENCE TO RELATED APPLICATIONS

This application claims the benefit of the filing date under 35 U.S.C. § 119(e) of U.S. Provisional Application For Patent Ser. No. 62/071,374 filed on Sep. 23, 2014 and U.S. Provisional Application For Patent Ser. No. 62/154,646 filed Apr. 29, 2015, both of which are incorporated herein by reference.

TECHNICAL FIELD

This disclosure relates to a biopsy needle; medical device incorporating the biopsy needle, and methods of using the biopsy needle and medical device to obtain a tissue sample.

BACKGROUND

In the field of human or veterinary medicine, it is often necessary to obtain a tissue sample for diagnosing the presence or extent of a disease. The tissue sample may be collected during open surgery or via the minimally invasive procedure known as percutaneous needle biopsy. The term "percutaneous" refers to any medical procedure where access to inner organs or other tissue is carried out by puncturing the skin with a needle as opposed to an approach where surgery is performed to expose the inner organs or tissue. Percutaneous biopsy is a procedure where a needle is passed through the skin to obtain a tissue sample. The excised tissue is then examined, typically under a microscope, and a diagnosis is made.

Core-needle biopsy is one type of percutaneous biopsy that involves removing a small sample of tissue using a hollow "core" needle. Typically, a core-biopsy needle has a two-part needle assembly comprising an outer coaxial sheath and an inner stylet. The distal ends of the outer coaxial sheath and inner stylet have a sharp tip that penetrates the tissue. The inner stylet also contains a sample tray region adjacent the sharp tip where tissue is collected.

When the stylet is deployed into tissue, the tissue is sliced and prolapses into the sample tray region. When the distal portion of the outer coaxial sheath is slid forward (distally) over the extended distal portion of the stylet, the prolapsed tissue in the sample tray region is completely severed from surrounding tissue and trapped in the sample tray region as the outer coaxial sheath completely surrounds the sample tray region of the stylet. Both the outer coaxial sheath and the inner stylet with the tissue sample secured therein are then removed from the patient. The outer coaxial sheath is then slid away from the distal end of the inner stylet to allow access and removal of the tissue sample from the sample tray region. The tissue may then be examined by a medical pathologist.

The inner stylet and outer coaxial sheath are typically contained within a spring-loaded firing device that first deploys the distal portion of inner stylet into the tissue of interest, followed immediately by the deployment of the distal portion of the outer coaxial sheath into the tissue. As the outer coaxial sheath axially slides over the extended distal portion of the stylet, the tissue of interest is severed and captured in the sample tray region. The captured tissue is undamaged and suitable for use as a biopsy sample.

Stylets of percutaneous biopsy needles known in the art are straight, rigid and do not bend when inserted into a target tissue. In fact, current developments by those skilled in the art are aimed at increasing the straightness and rigidity of the stylet to lessen or eliminate unwanted lateral "drift" of the stylet. Moreover, current improvements in core-biopsy needles include increasing the straightness and rigidity of the stylet in an attempt to reduce the tendency of the stylet to deflect when inserted into tissue.

Biopsy needles having a straight and rigid stylet typically require multiple insertions in order to obtain a sufficient tissue sample for the pathologist to make a definite diagnosis. Multiple insertions of the needles (i.e., both the inner stylet and the outer coaxial needles) increase the risk of complications such as infection, recovery time, patient discomfort, and is more likely to have an unsatisfactory cosmetic result. Accordingly, an important consideration in biopsy needle design is maximizing the biopsy size so that a definite diagnosis can be made with fewer insertions. There exists a substantial need in the art to provide a core-biopsy needle that can obtain a larger tissue sample compared known core-biopsy needles having straight and rigid stylets.

DETAILED DESCRIPTION

Figure 1:
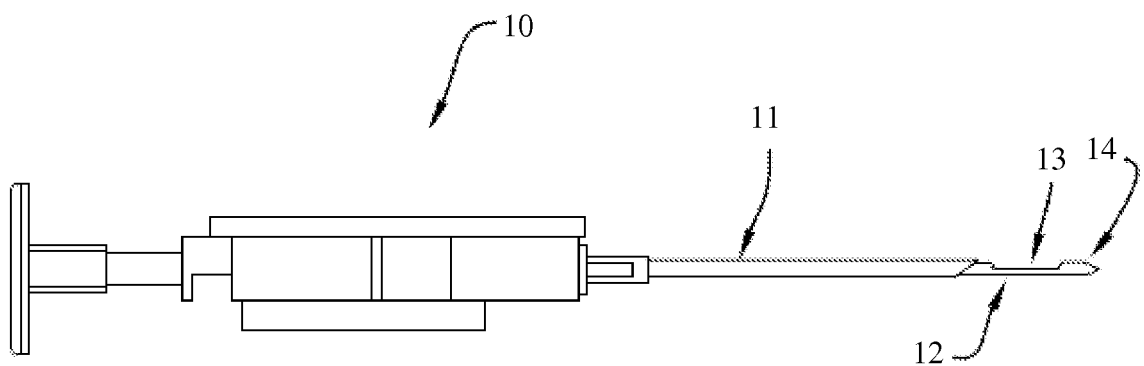
FIG. 1 is a side view of a known biopsy needle having a straight and rigid stylet in the open position ready to obtain a tissue sample.

Provided is a biopsy needle; medical device incorporating the biopsy needle, and methods of using the biopsy needle and medical device to obtain a sample of tissue for further analysis and testing.

In general, the biopsy needle comprises an outer coaxial sheath having opposite proximal and distal portions and a longitudinal axis extending therebetween, wherein the distal portion includes a tip portion and an opening; an inner stylet member having opposite proximal and distal ends and a longitudinal axis extending therebetween, wherein the distal portion includes a sample tray region and a tip portion; wherein the inner stylet is slidably engaged with the outer coaxial sheath between a first extended position and a second retracted position, wherein in the first extended position at least part of the distal portion of the inner stylet is bent or curved relative to the longitudinal axis of the outer coaxial sheath and in the second retracted position is substantially straight.

Although the biopsy needle described herein is applicable to any device used to obtain a representative sample of both biological and non-biological materials, the exemplary embodiments are implemented in the form of medical devices incorporating the biopsy needle to obtain a tissue sample. The medical device may include an outer coaxial sheath, an inner stylet, and deployment mechanism such as a handle or plunger. The proximal ends of both the outer coaxial sheath and the inner stylet are engaged with the deployment mechanism. The deployment mechanism allows the user to deploy the inner stylet distally into the tissue of interest, followed immediately by the deployment of the outer coaxial sheath into the tissue and around the distal portion of the stylet. As the outer coaxial sheath slides over the distal portion of the stylet, the tissue of interest is completely severed and captured in the sample tray region. The captured tissue is undamaged and suitable for use as a biopsy sample.

Additionally provided is a method for obtaining a tissue biopsy. The method comprises inserting the bent or curved (relative to the longitudinal axis of the coaxial sheath) distal portion of the inner stylet percutaneously to a biopsy site and capturing the prolapsed tissue in the sample tray region of the inner stylet, inserting the straight coaxial sheath percutaneously to the biopsy site to surround the sample tray region of the inner stylet, removing the outer coaxial sheath surrounding the sample tray region of the inner stylet containing the excised tissue, sliding the outer coaxial sheath away from the distal end of the inner stylet to allow access and removal of the tissue sample from the sample tray region.

Although the subject matter illustrated and described herein is embodied in a biopsy needle, medical device incorporating the biopsy needle, and methods of using the biopsy needle and medical device, it is not intended to be limited to these embodiments, since modifications may be made therein without departing from the spirit of the invention.

The biopsy needle may comprise an outer coaxial sheath that is movably or slidably engaged with an inner stylet for obtaining a tissue sample. The coaxial sheath slidably mounts around the inner stylet, allowing the coaxial sheath and inner stylet to move relative to one another between first extended and second retracted positions. In some embodiments, the outer coaxial sheath may be stationary while the inner stylet is movable. In some embodiments, the outer coaxial sheath may be movable while the inner stylet is stationary. In some embodiments, both the outer coaxial sheath and the inner stylet are movable in relation to one another.

The outer coaxial sheath and inner stylet have opposite proximal and distal ends and a longitudinal axis extending therebetween. As used throughout this specification, the term "proximal" refers to the end of the biopsy needle that is near the non-cutting end. As used throughout this specification, the term "distal" refers to the end of the biopsy needle that is the opposite end from the non-cutting end and is the end that is at least partially inserted into the patient to obtain the tissue sample.

The biopsy needle may comprise an outer coaxial sheath having a sharp distal tip and an inner stylet located at least partially within the outer coaxial sheath. The inner stylet and the outer coaxial sheath are movable along the longitudinal axis. The inner stylet has a sharp distal tip and a sample tray region adjacent the sharp tip for collecting the prolapsed tissue. The sample tray region of the inner stylet comprises a sample side and a non-sample side.

The coaxial sheath and/or inner stylet of the biopsy needle may comprise substantially similar or different materials. The coaxial sheath and/or inner stylet of the biopsy needle may comprise, but are not limited to, metals, alloys, polymers, plastics, composite materials, fiberglass, carbon fiber, graphene, carbyne or combinations thereof. Many other materials may be used depending on the environment and situation.

By way of illustration, but not in limitation, suitable alloys include stainless steel, nitinol, or other alloys that are known in the medical field as being appropriate for manufacturing biopsy needles and other medical instruments. According to certain illustrative embodiments, the coaxial sheath and/or inner stylet are at least partially manufactured from stainless steel.

The biopsy needle and medical device incorporating the biopsy needle may be automated, semi-automated, manual, or combinations thereof.

In some automated embodiments, the stylet and outer coaxial sheath are engaged with respective compression springs which are compressed via a cocking mechanism. When the stylet is in the desired position, it is deployed or "fired" into the tissue of interest, causing the severed tissue to prolapse into the sample tray region. Once the inner stylet has reached its full deployment length, the biopsy device automatically deploys the outer coaxial sheath over the stylet to cut and trap the prolapsed tissue in the sample tray region on the stylet. The trigger mechanism releases the inner stylet and the outer coaxial sheath in rapid sequence into the tissue to be collected.

In some embodiments, the inner stylet and coaxial sheath are operatively connected to a drive assembly which selectively moves the inner stylet and coaxial sheath between their respective first extended and second retracted positions. The drive assembly may be spring-loaded, motorized, or fired using some other type of mechanism currently known in the medical device field. The drive mechanisms are configured to deploy the inner stylet in a single cutting stroke from the coaxial sheath into the tissue, i.e., the first extended position, and then substantially simultaneously deploy the coaxial sheath in a single cutting stroke to surround the sample tray region on the inner stylet, i.e., the second retracted position, thereby capturing the excised tissue.

In some semi-automated embodiments, the stylet is manually advanced into the tissue of interest followed by the automatic deployment of the outer coaxial sheath to capture the prolapsed tissue inside the sample tray region.

In some manual embodiments, the stylet is manually deployed into the tissue of interest followed by manually deploying the outer coaxial sheath to capture the prolapsed tissue inside the sample tray region.

In some embodiments, at least part of the inner stylet at the first extended position is at a bend angle of about 90 degrees or less relative to the outer coaxial sheath. In some embodiments, at least part of the inner stylet at the first extended position is at a bend angle of about 80 degrees or less relative to the outer coaxial sheath. In some embodiments, at least part of the inner stylet at the first extended position is at a bend angle of about 70 degrees or less relative to the outer coaxial sheath. In some embodiments, at least part of the inner stylet at the first extended position is at a bend angle of about 60 degrees or less relative to the outer coaxial sheath. In some embodiments, at least part of the inner stylet at the first extended position is at a bend angle of about 50 degrees or less relative to the outer coaxial sheath. In some embodiments, at least part of the inner stylet at the first extended position is at a bend angle of about 40 degrees or less relative to the outer coaxial sheath. In some embodiments, at least part of the inner stylet at the first extended position is at a bend angle of about 30 degrees or less relative to the outer coaxial sheath. In some embodiments, at least part of the stylet at the first extended position is at a bend angle of about 20 degrees or less relative to the outer coaxial sheath. In some embodiments, at least part of the inner stylet at the first extended position is at a bend angle of about 10 degrees or less relative to the outer coaxial sheath.

In some embodiments, at least part of the stylet at the first extended position has a radius of curvature of greater than 0 to about 20 mm relative to the longitudinal axis of said coaxial sheath. In addition, a suitable radius of curvature or other forms of curvature for the distal portion of the inner stylet will be apparent to those of ordinary skill in the art in view of the teachings herein.

The bend or curve in the stylet allows a larger tissue sample to be collected as compared to known biopsy needles having a straight and rigid stylet. It has unexpectedly been found that the greater the sample tray is bent or curved relative to the longitudinal axis of the outer coaxial sheath, the larger the tissue sample that may be collected. Reducing the number of insertions a patient must endure is a significant advantage of the biopsy needle. In addition, the increased biopsy size provided by the biopsy needle allows the physician to use smaller needle gauges resulting in minimum patient discomfort.

One element of the biopsy needle is the ability of the inner stylet to bend or curve relative to the longitudinal axis of the coaxial sheath, but return to a substantially straight position when refracted into the coaxial sheath. That is, when retracted into the outer coaxial sheath, the distal portion of the stylet assumes a substantially parallel position relative to the longitudinal axis of the outer coaxial sheath.

In addition to the larger tissue samples obtained, the biopsy needle unexpectedly provides the user with enhanced control of the direction of the needle during use. The bend or curve permits the user to steer the stylet in the desired direction, which allows the user to obtain a larger sample from the direction of the bend as well as what is directly in front of the coaxial sheath.

The sample tray region of the stylet may include one or more grooves, indentations, or recesses that are formed on the sample side of the sample tray region. According to certain illustrative embodiments, the biopsy needle comprises an inner stylet having a sample tray region including one or more hemispherical, hemicylindrical or V-shaped grooves formed on the sample side of the sample tray region.

According to certain illustrative embodiments, the one or more grooves, indentations or recesses may extend longitudinally along a portion of the longitudinal axis of the sample tray region. According to some embodiments, the grooves, indentations, or recesses extend along the entire length of the sample tray region.

The one or more grooves, indentations or recesses extend into the thickness of the sample tray region on the stylet, thereby increasing the area of the sample tray region and allowing for a larger tissue sample to be collected.

The distal end of the outer coaxial sheath comprises a leading edge and a trailing edge defining an opening. In some embodiments, recessed portions exist between the opposite lateral sides of the leading and trailing edges to facilitate the ease with which the distal portion of the inner stylet made extend from and retract into the coaxial sheath.

Inner stylet tip portions of known biopsy needles typically have a leading edge (i.e., the sharp edge that penetrates/cuts tissue) that extends upwardly and proximally and transitions into a longitudinally and proximally extending relatively long plateau area, e.g., 5-10 mm, which then terminates downwardly into the sample tray region. The relatively long plateau area of known biopsy needles unnecessarily increases the "dead space" of the tip portion. As used herein, the term "dead space" refers to the area of the tip portion that could otherwise be part of the sample tray region without effecting the ability of the sample tray region to collect tissue samples.

In some embodiments, the tip portion of the stylet has a relatively short plateau as compared to the plateau length of known style tip portions. In such embodiments, the length of the longitudinally extending plateau area is about 5 mm or less. In other embodiments, the length of the longitudinally extending plateau area is about 4 mm or less. In other embodiments, the length of the longitudinally extending plateau area is about 3 mm or less. In other embodiments, the length of the longitudinally extending plateau area is about 2 mm or less. In other embodiments, the length of the longitudinally extending plateau area is about 1 mm or less.

In some embodiments, the tip portion of the stylet has virtually no longitudinally extending plateau area. In such embodiments, the leading edge upwardly and proximally extends to an apex and then terminates downwardly into the sample tray region.

The longitudinally extending plateau area of the stylet tip portion is typically the full diameter of the stylet body, thus the tissue must travel over the entire length of the plateau area before it can prolapse into the sample tray region. By reducing or eliminating the length of the plateau area, the area of the sample tray region is increased and a larger sample may be collected. It has surprisingly been found that such a configuration does not negatively effect the ability of the sample tray region to collect tissue samples, yet results in larger samples.

Additionally, the short or virtually non-existent plateau area of the stylet tip portion of the biopsy needle allows the user to obtain a tissue sample without having to penetrate too far into the tissue to be sampled or having to penetrate beyond the sample being biopsied.

The tip portion of the outer coaxial sheath may be oriented such that the tip moves across the opening of the sample tray region on the stylet so as to achieve effective cutting of surrounding tissue outside the sample tray region.

The tip portions of the inner stylet and coaxial sheath may include different tip angles and/or orientations. The tips may be a multi-faced sharpened point. The amount of faces may be variable. In some embodiments, the tip portions of the inner stylet and/or the outer coaxial sheath have a diamond or bevel shaped.

The distal tip of the coaxial sheath may be etched to produce a rough surface so the needle may be seen with ultrasound imaging.

In some embodiments, the biopsy needle comprises an inner stylet wherein at least one hinge and/or a joint is positioned proximal the sample tray region. In some embodiments, the biopsy needle comprises an inner stylet wherein at least one hinge and/or a joint is positioned on at least part of the sample tray region.

The at least one hinge or joint allows the distal portion of the stylet to be bent or curved when inserted into the tissue. The at least one hinge or joint allows the user to position the stylet at the desired angle for each individual biopsy. The hinge or joint may be substantially the same or different material as compared to the remainder of the stylet. In some embodiments, the hinge or joint may be a flexible material. In some embodiments, the hinge or joint may be of a different thickness as compared to the remainder of the stylet to facilitate bending of the stylet.

It is possible to obtain a larger tissue size with the presently disclosed biopsy needle comprising a bent or curved distal portion of the stylet compared to the straight, rigid and non-bendable stylets found in known biopsy needles. As a result of the larger samples collected from the biopsy needle, the diameter of the biopsy needle can be made very small, yet still obtain sufficient sample sizes.

The biopsy needle may be used for obtaining a sample of many different types of bodily tissues. For example, and only by way of illustration, the biopsy needle may be used to obtain samples of all soft tissues. Without limitation, the biopsy needle may be used to obtain tissue samples from lung, kidney, liver and breast with the advantage of obtaining larger samples. The biopsy needle is not limited to human use and may be used to obtain a representative sample of any material, both biological and non-biological.

The biopsy needle and medical device is readily understood when read in conjunction with illustrative FIGS. 1-10. It should be noted that the biopsy needle and medical device are not limited to any of the illustrative embodiments shown in the drawing figures, but rather should be construed in breadth and scope in accordance with the disclosure provided herein.

FIG. 1 is a side view of a prior art biopsy needle 10. Biopsy needle 10 includes an outer coaxial sheath 11 having opposite proximal and distal ends. Outer coaxial sheath 11 is coaxially positioned about an inner stylet 12. Inner stylet 12 also includes proximal and distal ends. Located near the distal end of inner stylet 12 is the sample tray region 13 that is formed near the distal end of the stylet 12. Distal end of inner stylet 12 terminates in a tip portion 14.

Figure 2:
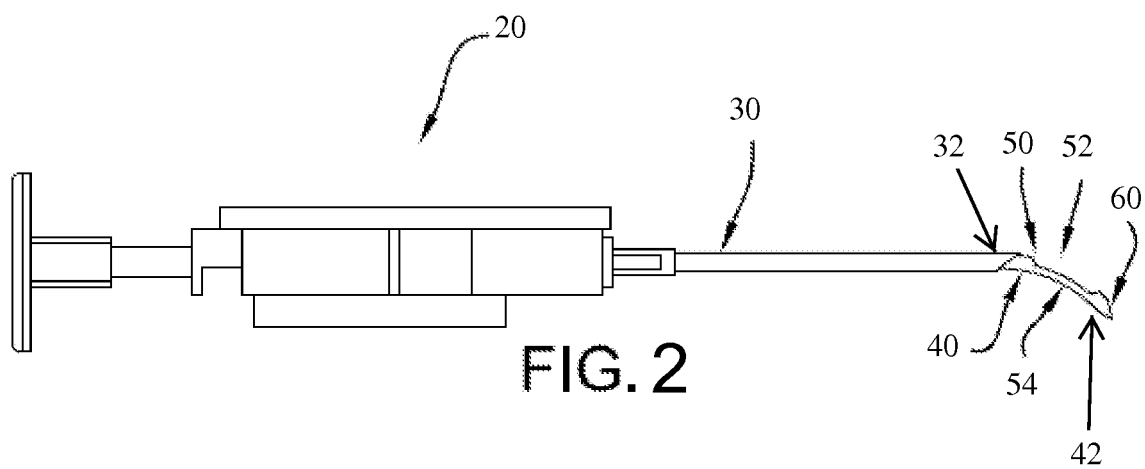
FIG. 2 is a side view of one illustrative embodiment of the biopsy needle showing the stylet in the "bent" or "curved" open position ready to obtain a tissue sample.

FIG. 2 is a side view of the biopsy needle 20. Biopsy needle 20 includes an outer coaxial sheath 30 having opposite proximal (not shown) and distal 32 ends. Outer coaxial sheath 30 is coaxially positioned about inner stylet 40. Inner stylet 40 also includes proximal (not shown) and distal 42 ends. Located near the distal end 42 of inner stylet 40 is the sample tray region 50 that is formed in one side of the stylet 40. Sample tray region 50 comprises a flattened region of the inner stylet 40 and includes opposite facing sample side 52 and non-sample side 54. The distal portion of the inner stylet 42, including the sample tray region 50, is shown in a bent or curved position relative to the longitudinal axis of the coaxial sheath 30. The tip portion 60 of the inner stylet 40 has a stop surface that is engaged with a stop surface of the distal end 32 of the outer coaxial sheath 30.

Figure 3:
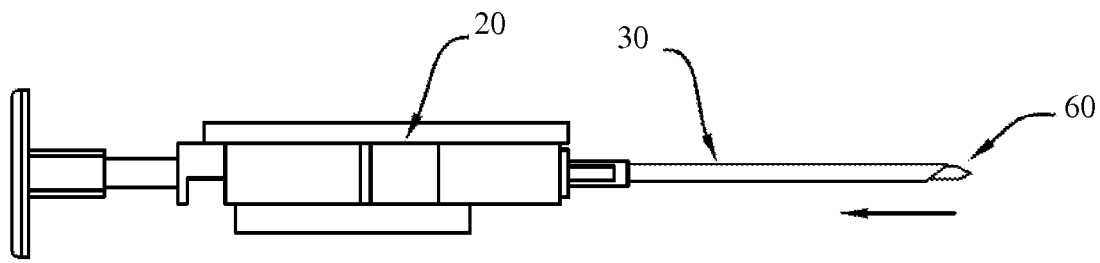
FIG. 3 is a side view of the biopsy needle of FIG. 2 in the closed position after the tissue sample has been captured and the sample tray region of the stylet has been retracted into the lumen of the coaxial sheath of the biopsy needle.

FIG. 3 is a side view of the biopsy needle 20 of FIG. 1 with the sample tray region (not shown) retracted into the lumen of the outer coaxial sheath 30. The tip portion 60 at the distal end of the inner stylet has a stop surface that is engaged with a stop surface of the distal end of the outer coaxial sheath 30.

Figure 4:
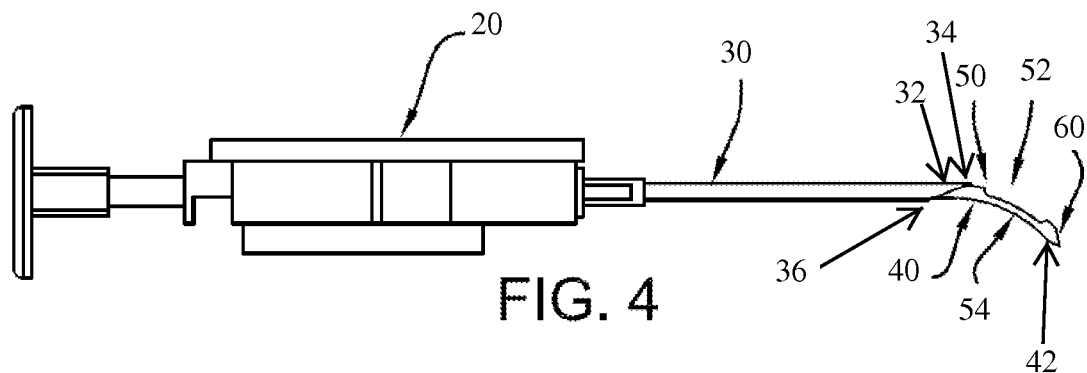
FIG. 4 is a side view of one illustrative embodiment of the biopsy needle showing the leading and trailing edges defining an opening at the distal end of the coaxial sheath, wherein between the opposite lateral sides of the leading and trailing edges recessed portions facilitate the movement of the stylet extending from and retracting into the coaxial sheath.

FIG. 4 is a side view of the biopsy needle 20. Biopsy needle 20 includes an outer coaxial sheath 30 having opposite proximal (not shown) and distal 32 ends. Outer coaxial sheath 30 is coaxially positioned about inner stylet 40. Inner stylet 40 also includes proximal (now shown) and distal 42 ends. Located near the distal end 42 of inner stylet 40 is the sample tray region 50 that is formed in one side of the stylet 40. Sample tray region 50 comprises a flattened region of the inner stylet 40 and includes opposite facing sample side 52 and non-sample side 54. The distal portion of the inner stylet 42, including the sample tray region 50, is shown with in a bent or curved position relative to the longitudinal axis of the coaxial sheath 30. Distal portion 32 of outer coaxial sheath 30 comprises a leading edge 34 and a trailing edge 36 defining an opening. Between the opposite lateral sides of the leading 34 and trailing 36 edges are recessed portions to facilitate the ease with which the distal portion 42 of the inner stylet 40 may extend from and retract into said coaxial sheath 30.

Figure 4A:
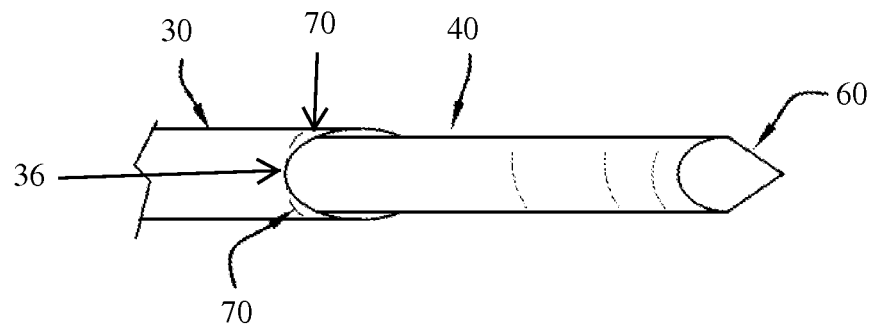
FIG. 4A is a partial perspective bottom view of FIG. 4 showing the leading and trailing edges defining an opening at the distal end of the coaxial sheath, wherein between the opposite lateral sides of the leading and trailing edges recessed portions facilitate the movement of the stylet extending from and retracting into the coaxial sheath.

FIG. 4A is a partial bottom view of FIG. 4 showing the recessed portions 70 opposite lateral sides of the leading 34 and trailing 36 edges to facilitate the ease with which the distal portion 42 of the inner stylet 40 may extend from and retract into said coaxial sheath 30.

Figure 5:
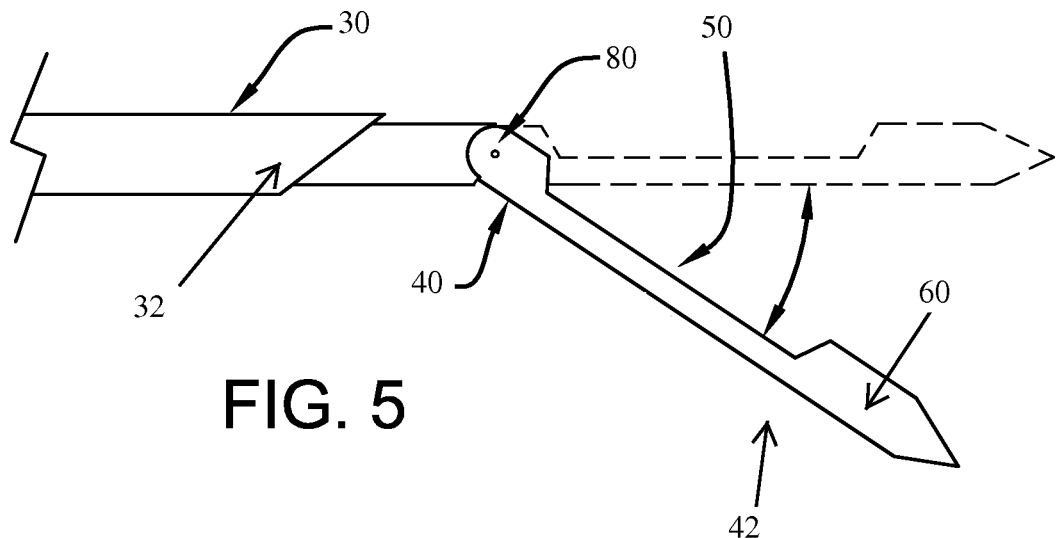
FIG. 5 is a partial perspective side view of one illustrative embodiment of the biopsy needle with at least one hinge or joint proximal the sample tray region.

FIG. 5 is a partial perspective side view the biopsy needle 20. Biopsy needle 20 includes an outer coaxial sheath 30 having opposite proximal (not shown) and distal 32 ends. Outer coaxial sheath 30 is coaxially positioned about inner stylet 40. Inner stylet 40 also includes proximal (not shown) and distal 42 ends. Located near the distal 42 end of inner stylet 40 is the sample tray region 50 that is formed in one side of the stylet 40. Sample tray region 50 comprises a flattened region of the inner stylet 40 and includes opposite facing sample side and non-sample side. At least one hinge or joint 80 positioned proximal the sample tray region 50 permits the distal end 42 of the inner stylet 40, including the sample tray region 50 to be in a bent position relative to the longitudinal axis of the coaxial sheath 30.

Figure 6:
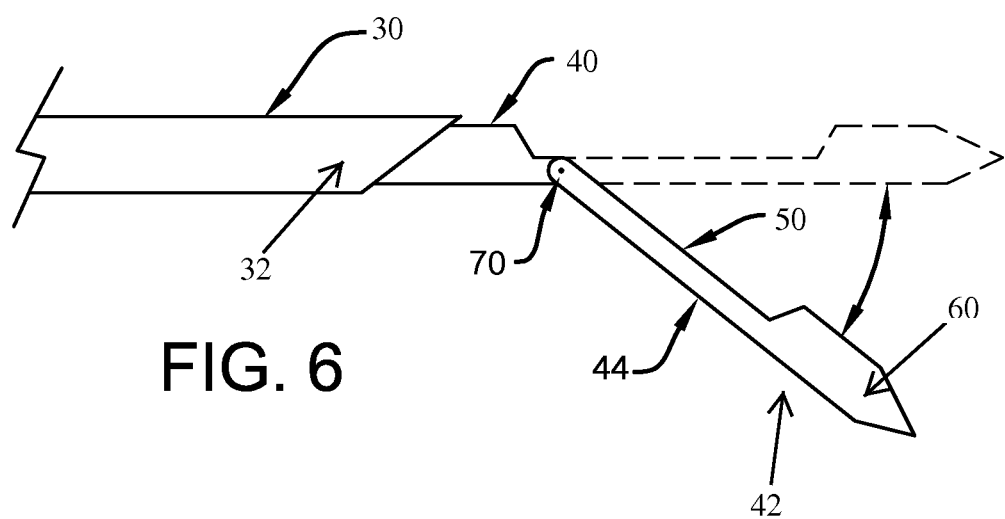
FIG. 6 is a partial perspective side view of one illustrative embodiment of the biopsy needle with at least one portion of the sample tray region of the inner stylet having at least one hinge or joint engaged thereon.

FIG. 6 is a partial perspective side view the biopsy needle 20. Biopsy needle 20 includes an outer coaxial sheath 30 having opposite proximal (not shown) and distal 32 ends. Outer coaxial sheath 30 is coaxially positioned about inner stylet 40. Inner stylet 40 also includes proximal (not shown) and distal 42 ends. Located near the distal 42 end of inner stylet 40 is the sample tray region 50 that is formed in one side of the stylet 40. Sample tray region 50 comprises a flattened region of the inner stylet 40 and includes opposite facing sample side and non-sample side. At least one portion of sample tray region 50 has at least one hinge or joint 70 engaged thereon to permit the sample tray region 50 to be in a bent position relative to the longitudinal axis of the coaxial sheath 30

Figure 7:
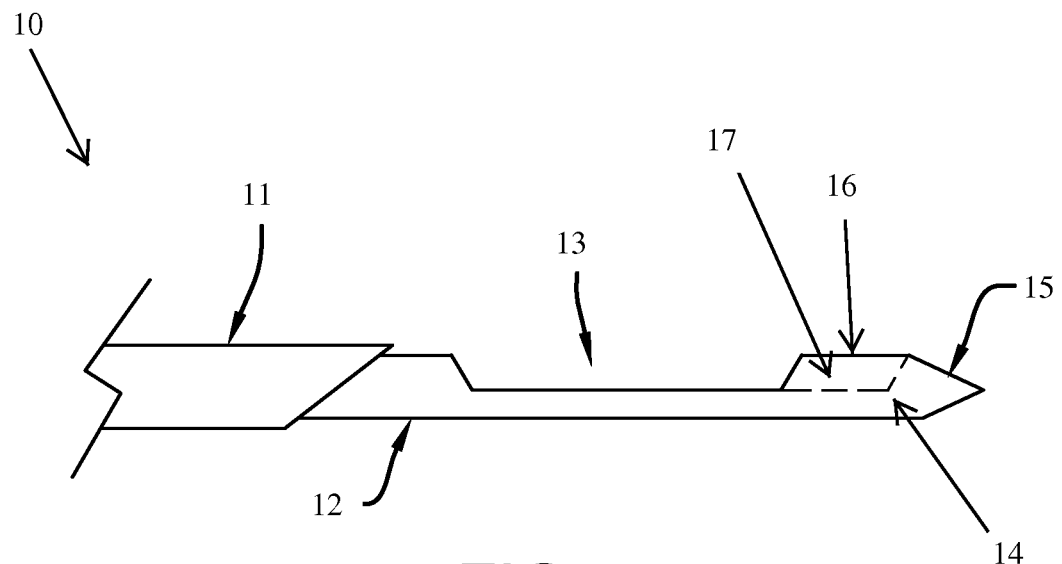
FIG. 7 is a partial perspective side view of a known biopsy needle showing a stylet tip portion having a leading edge upwardly and proximally extending to a relatively long plateau area, e.g., 5-10 mm, that extends longitudinally and proximally relative to the longitudinal axis of the stylet and terminates downwardly into the sample tray region.

FIG. 7 is a partial side view of a known biopsy needle 10 of FIG. 1 having a leading edge 15 that upwardly and proximally extends to a relatively long plateau area 16 that extends longitudinally and proximally, and terminates downwardly into the sample tray region 13. The relatively long plateau area 16 unnecessarily increases the "dead space" 17 of the tip portion 14.

Figure 8:
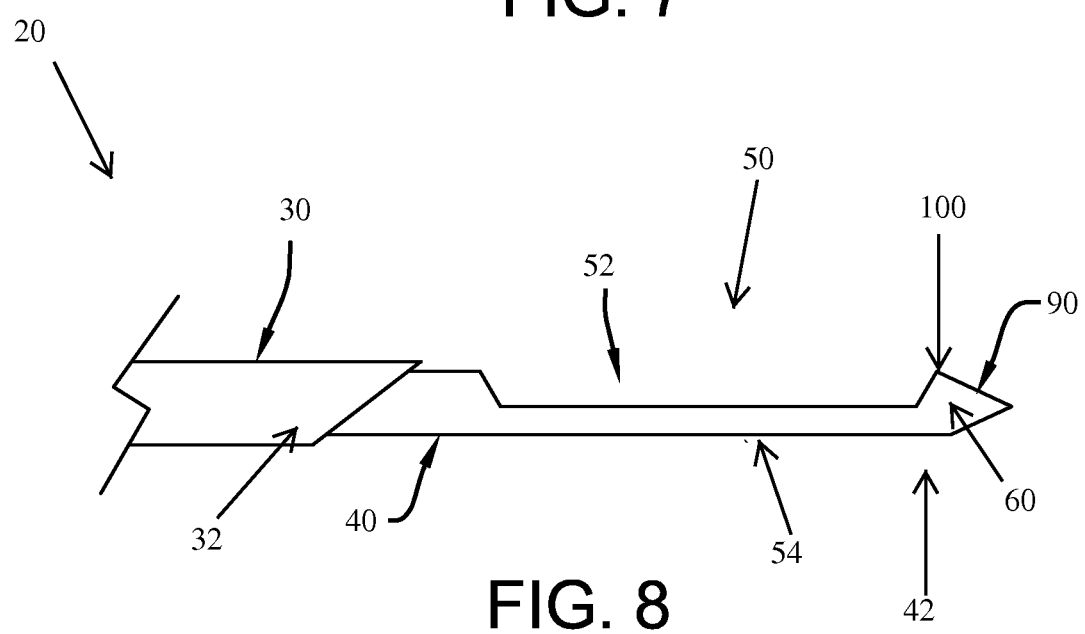
FIG. 8 is a partial perspective side view of one illustrative embodiment of the biopsy needle showing a stylet tip portion having a leading edge that upwardly and proximally extends to an apex and terminates downwardly into the sample tray region.

FIG. 8 is a partial side view of the biopsy needle 20. Biopsy needle 20 includes an outer coaxial sheath 30 having opposite proximal (not shown) and distal 32 ends. Outer coaxial sheath 30 is coaxially positioned about inner stylet 40. Inner stylet 40 also includes proximal (not shown) and distal 42 ends. Located near the distal 42 end of inner stylet 40 is the sample tray region 50 that is formed in one side of the stylet 40. Sample tray region 50 comprises a flattened region of the inner stylet 40 and includes opposite facing sample side 52 and non-sample side 54. Stylet tip portion has a leading edge 90 that upwardly and proximally extends to an apex 100, and then terminates downwardly into the sample tray region 50.

Figure 9:
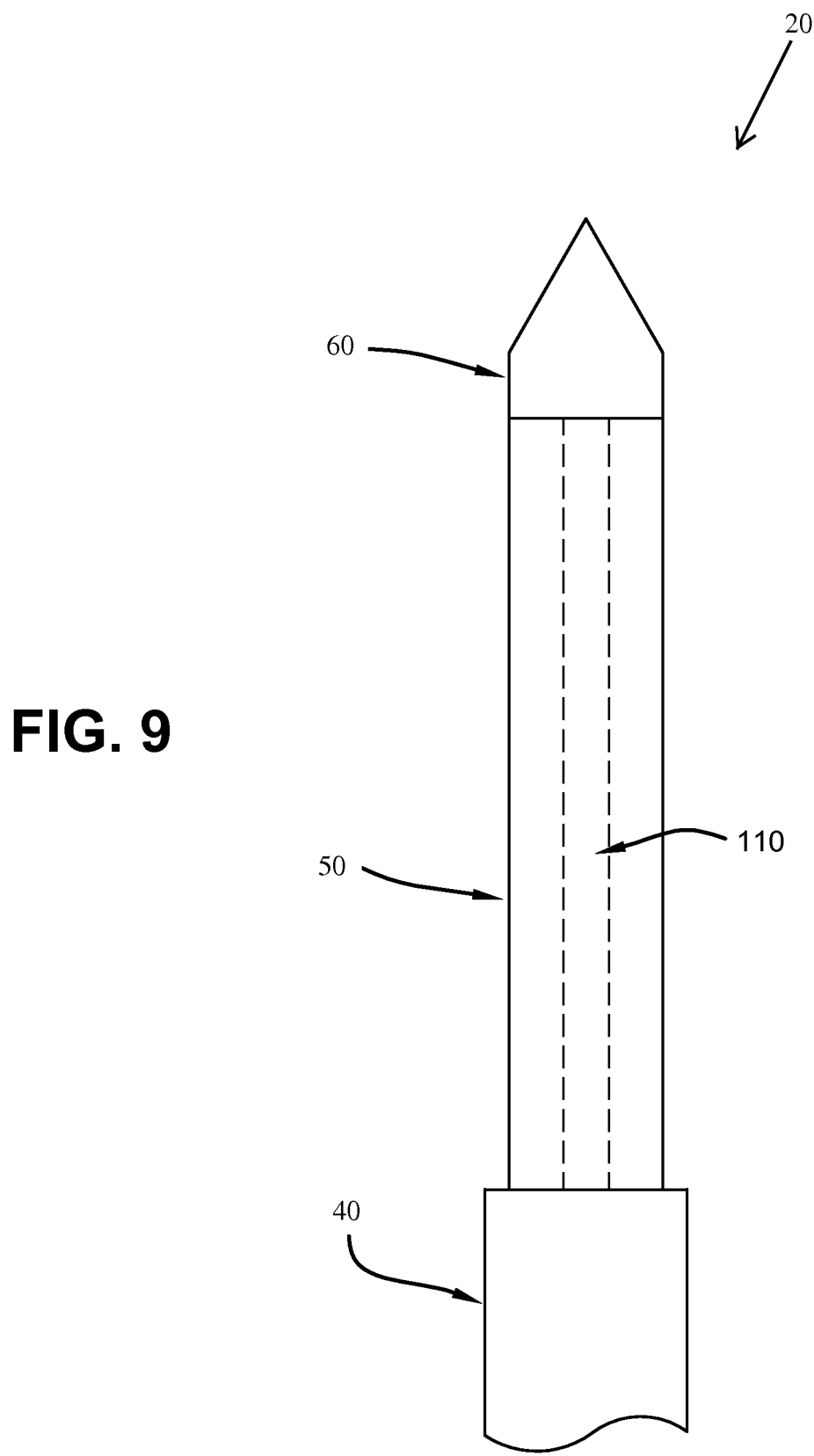
FIG. 9 is a partial top view of one illustrative embodiment of the biopsy needle with the sample tray region of the stylet having a longitudinally extending groove formed on the sample side of the flattened surface.

FIG. 9 is a partial top view of the biopsy needle 20 with the sample tray region 50 of the stylet 40 having a longitudinally extending groove 110 formed on the sample side of the flattened surface.

Figure 10A:
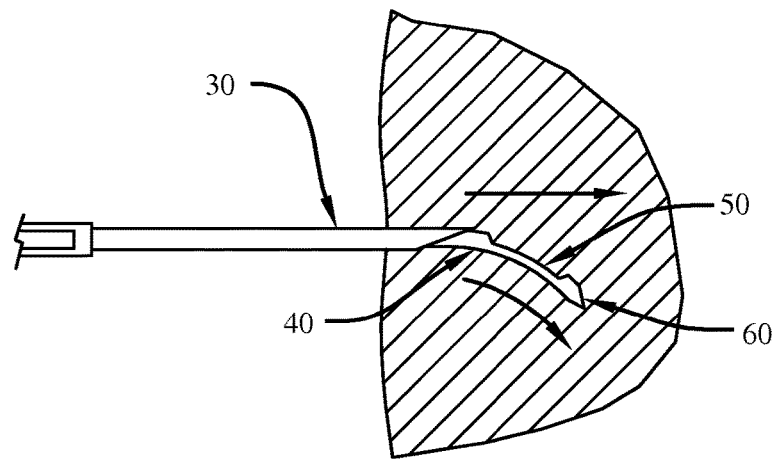
FIGS. 10A and 10B are partial perspective side views of illustrative embodiments of the biopsy needle showing the bent or curved distal portion of the inner stylet and the straight outer coaxial sheath being deployed into a tissue of interest and capturing the excised tissue in the sample tray region.

FIG. 10A is a partial side view showing an illustrative embodiment of the biopsy needle in operation deploying the inner stylet 40 into a target tissue.

Figure 10B:
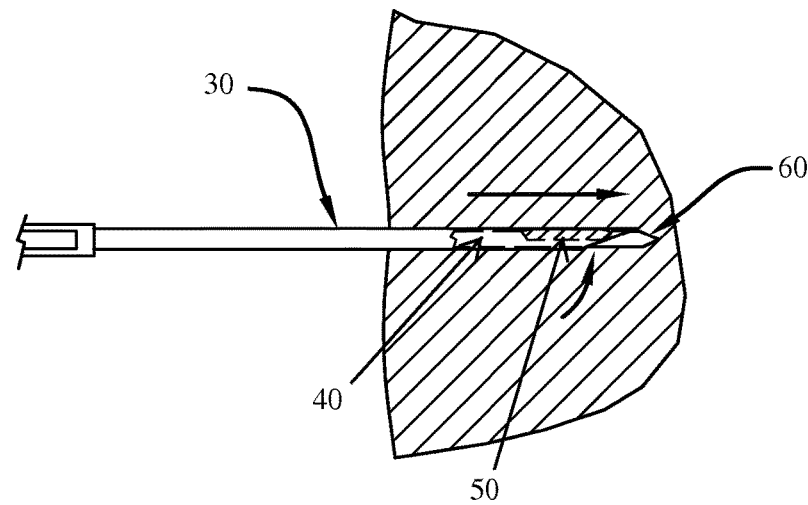

FIG. 10B is a partial side view showing an illustrative embodiment of the biopsy needle in operation with the outer coaxial sheath 30 positioned around the inner stylet 40 to capture the excised tissue in the sample tray region 50.

The method of obtaining a tissue sample with the biopsy needle will now be demonstrated by the following non-limiting illustrative example of its use and application.

EXAMPLES

Twenty-four tissue samples were collected from bovine liver using a 14 gauge prior art biopsy needle having a straight and rigid inner stylet. This same procedure was repeated using the presently disclosed biopsy needle having a curved inner stylet relative to the longitudinal axis of the coaxial sheath. The sizes and dimensions of the samples collected are summarized in Table 1.

TABLE 1

| Example No. | Bovine Liver Prior Art Biopsy Needle | | | Bovine Liver Inventive Biopsy Needle | | |
|---|---|---|---|---|---|---|
| | Mass (g) | Length (mm) | Width (mm) | Mass (g) | Length (mm) | Width (mm) |
| 1 | 0.02 | 2.4 | 0.15 | 0.024 | 1.5 | 0.3 |
| 2 | 0.033 | 2.3 | 0.15 | 0.029 | 2.1 | 0.25 |
| 3 | 0.028 | 2.2 | 0.14 | 0.029 | 2 | 0.2 |
| 4 | 0.033 | 2 | 0.14 | 0.04 | 2.2 | 0.3 |
| 5 | 0.014 | 2.1 | 0.15 | 0.033 | 2.3 | 0.3 |
| 6 | 0.011 | 1 | 0.1 | 0.031 | 1.7 | 0.2 |
| 7 | 0.018 | 1.8 | 0.1 | 0.035 | 3.1 | 0.2 |
| 8 | 0.032 | 2.4 | 0.1 | 0.035 | 3.2 | 0.2 |
| 9 | 0.18 | 1.4 | 0.1 | 0.033 | 2.2 | 0.2 |
| 10 | 0.01 | 1.2 | 0.12 | 0.025 | 2.1 | 0.2 |
| 11 | 0.009 | 1.3 | 0.2 | 0.031 | 2.4 | 0.2 |
| 12 | 0.012 | 2.1 | 0.1 | 0.033 | 1.2 | 0.2 |
| 13 | 0.019 | 2.2 | 0.12 | 0.032 | 2.2 | 0.1 |
| 14 | 0.01 | 2 | 0.12 | 0.032 | 1.5 | 0.2 |
| 15 | 0.022 | 2 | 0.2 | 0.016 | 2.2 | 0.2 |
| 16 | 0.025 | 1.2 | 0.15 | 0.027 | 2.2 | 0.1 |
| 17 | 0.021 | 2.4 | 0.1 | 0.026 | 2 | 0.2 |
| 18 | 0.0006 | 2.2 | 0.2 | 0.021 | 1.3 | 0.2 |
| 19 | 0.018 | 2.4 | 0.2 | 0.031 | 1.7 | 0.2 |
| 20 | 0.012 | 2.7 | 0.15 | 0.017 | 2 | 0.3 |
| 21 | 0.015 | 1.7 | 0.1 | 0.024 | 2.1 | 0.3 |
| 22 | 0.01 | 1.5 | 0.1 | 0.017 | 2.2 | 0.2 |
| 23 | 0.012 | 2.1 | 0.15 | 0.02 | 2.5 | 0.2 |
| 24 | 0.019 | 1.7 | 0.15 | 0.025 | 3.1 | 0.2 |

The average length of the 24 samples collected using the prior art biopsy needle having a straight stylet was 1.9 cm as compared to 2.1 cm using the presently described biopsy needle. The average width of the 24 samples collected using the prior art biopsy needle having a straight stylet was 0.13 cm as compared to 0.21 cm using the presently described biopsy needle. The average mass of the 24 samples collected using the prior art biopsy needle having a straight stylet was 0.024 g as compared to 0.027 g using the using the presently described biopsy needle. These tests show that a biopsy needle having a curved stylet relative to the longitudinal axis of the coaxial sheath allows for a larger biopsy size to be obtained in all respects (i.e., length, width and mass) as compared biopsies collected using a prior art biopsy needle having a straight and rigid inner stylet.

While the biopsy needle, medical devices incorporating the biopsy needle, and methods of using the biopsy needle and medical devices have been described in connection with various embodiments, it is to be understood that other similar embodiments may be used or modifications and additions may be made to the described embodiments for performing the same function. Furthermore, the various illustrative embodiments may be combined to produce the desired results. Therefore, the biopsy needle, medical devices incorporating the biopsy needle, and methods of using the biopsy needle and medical devices should not be limited to any single embodiment.

It will be understood that the embodiments described herein are merely exemplary, and that one skilled in the art may make variations and modifications without departing from the spirit and scope of the invention. All such variations and modifications are intended to be included within the scope of the invention as described hereinabove. Further, all embodiments disclosed are not necessarily in the alternative, as various embodiments of the invention may be combined to provide the desired result.

What is claimed:

1. A biopsy needle comprising: a straight outer coaxial cutting sheath having opposite proximal and distal portions and a longitudinal axis extending therebetween, wherein said outer coaxial sheath is always straight, said distal portion of said straight outer coaxial cutting sheath comprises a tip portion and an opening; an inner stylet having opposite proximal and distal ends and a longitudinal axis extending therebetween, said distal portion of said inner stylet comprises a sample tray region and a tip portion; wherein the inner stylet is slidably engaged with the straight outer coaxial cutting sheath between a first extended position and a second retracted position, wherein in the extended position the entire distal portion of said inner stylet is bent, hinged or curved relative to said straight outer coaxial cutting sheath; wherein the tip portion of said inner stylet comprises a leading edge extending upwardly and proximally and transitions into a longitudinally and proximally extending plateau having a length of 5 mm or less.

2. The biopsy needle of claim 1, wherein the entire distal portion of said stylet at said first extended position is at a bend angle of 90 degrees or less relative to the straight outer coaxial cutting sheath.

3. The biopsy needle of claim 2, wherein the entire distal portion of said stylet at said first extended position is at a bend angle of 70 degrees or less relative to the straight outer coaxial cutting sheath.

4. The biopsy needle of claim 2, wherein the entire distal portion of said stylet at said first extended position is at a bend angle of 50 degrees or less relative to the straight outer coaxial cutting sheath.

5. The biopsy needle of claim 2, wherein the entire distal portion of said stylet at said first extended position is at a bend angle of 30 degrees or less relative to the straight outer coaxial cutting sheath.

6. The biopsy needle of claim 2, wherein the entire distal portion of said stylet at said first extended position is at a bend angle of 10 degrees or less relative to the straight outer coaxial cutting sheath.

7. The biopsy needle of claim 1, wherein the entire distal portion of said stylet at said first extended position has a radius of curvature of greater than 0 up to 20 mm relative to said straight coaxial cutting sheath.

8. The biopsy needle of claim 1, wherein said at least part of said stylet comprises a joint proximal the sample tray region, wherein said joint permits at least part of said stylet to pivot relative to said straight coaxial cutting sheath.

9. The biopsy needle of claim 1, wherein said at least part of said stylet comprises a joint on at least a portion of said sample tray region of said stylet, wherein said joint permits at least part of said sample tray region to pivot relative to said coaxial cutting sheath.

10. The biopsy needle of claim 1, wherein said sample tray region comprises a groove, indentation and/or recess formed on a sample side of said sample tray region.

11. The biopsy needle of claim 10, wherein said groove, indentation and/or recess is hemispherical, hemicylindrical or V-shaped.

12. The biopsy needle of claim 10, wherein said groove, indentation and/or recess extend longitudinally along a portion of the longitudinal axis of said sample tray region.

13. The biopsy needle of claim 10, wherein said groove, indentation and/or recess extend longitudinally along the entire length of said sample tray region.

14. The biopsy needle of claim 1, wherein said distal portion of said straight outer coaxial cutting sheath comprises a leading edge and a trailing edge defining an opening, wherein between opposite lateral sides of said leading and trailing edges recessed portions facilitate movement of the distal portion of said inner stylet between the first extended position and the second retracted position.

15. The biopsy needle of claim 1, wherein the length of said plateau is 4 mm or less.

16. The biopsy needle of claim 1, wherein length of said plateau is 2 mm or less.

17. The biopsy needle of claim 1, wherein the length of said plateau is 1 mm or less.

18. The biopsy needle of claim 1, wherein said sample tray region is V-shaped.

19. A medical device comprising: a straight outer coaxial cutting sheath having opposite proximal and distal portions and a longitudinal axis extending therebetween, wherein said outer coaxial sheath is always straight, said distal portion of said straight outer coaxial cutting sheath comprises a tip portion and an opening; an inner stylet member having opposite proximal and distal ends and a longitudinal axis extending therebetween, said distal portion of said inner stylet comprises a sample tray region and a tip portion; wherein the inner stylet is slidably engaged with said straight outer coaxial cutting sheath between a first extended position and a second retracted position, wherein in the extended position the entire distal portion of said inner stylet is bent, hinged or curved relative to said straight outer coaxial cutting sheath; and a deployment mechanism engaged with said straight outer coaxial cutting sheath and inner stylet, wherein said deployment mechanism is capable of deploying said inner stylet distally into a tissue in said first extended position, followed by the deployment of said outer coaxial sheath into said tissue to axially slide over said extended distal portion of said stylet, wherein the deployment of said outer coaxial sheath severs and captures the tissue located in said sample tray region of said inner stylet and returns said inner stylet to said second retracted position; wherein the tip portion of said inner stylet comprises a leading edge extending upwardly and proximally and transitions into a longitudinally and proximally extending plateau having a length of 5 mm or less.

20. A method for obtaining a sample of material comprising: inserting a bent, hinged or curved inner stylet, relative to a straight outer coaxial cutting sheath, wherein the entire distal portion of the inner stylet is bent, hinged or curved relative to the straight outer coaxial cutting sheath, into said material and capturing said material in a sample tray region of said inner stylet, inserting said straight outer coaxial cutting sheath into said material to axially slide over said stylet, wherein the inserting of said outer coaxial sheath severs the material located in said sample tray region of said inner stylet, removing said straight outer coaxial cutting sheath that surrounds said sample tray region of said inner stylet containing said material, sliding the straight outer coaxial cutting sheath away from the distal end of said inner stylet to allow access and removal of said material from said sample tray region, wherein said outer coaxial sheath is straight; wherein a tip portion of said inner stylet comprises a leading edge extending upwardly and proximally and transitions into a longitudinally and proximally extending plateau having a length of 5 mm or less.

\* \* \* \* \*